US006989241B2

(12) United States Patent
Esmon et al.

(10) Patent No.: US 6,989,241 B2
(45) Date of Patent: Jan. 24, 2006

(54) ASSAY FOR RAPID DETECTION OF HUMAN ACTIVATED PROTEIN C AND HIGHLY SPECIFIC MONOCLONAL ANTIBODY THEREFOR

(75) Inventors: Charles T. Esmon, Oklahoma City, OK (US); Patricia C. Y. Liaw, Hamilton (CA); Gary L. Ferrell, McLoud, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 65 days.

(21) Appl. No.: 10/398,063

(22) PCT Filed: Oct. 2, 2001

(86) PCT No.: PCT/US01/30802

§ 371 (c)(1),
(2), (4) Date: Jul. 10, 2003

(87) PCT Pub. No.: WO02/29015

PCT Pub. Date: Apr. 11, 2002

(65) Prior Publication Data

US 2004/0014138 A1    Jan. 22, 2004

Related U.S. Application Data

(60) Provisional application No. 60/237,481, filed on Oct. 2, 2000.

(51) Int. Cl.
*G01N 33/573* (2006.01)
*G01N 33/577* (2006.01)

(52) U.S. Cl. .................. 435/7.4; 435/337; 436/512; 436/518; 436/548; 530/388.25

(58) Field of Classification Search ............... 435/7.4, 435/337; 436/512, 518, 548; 530/388.25
See application file for complete search history.

(56) References Cited

FOREIGN PATENT DOCUMENTS

EP        00287028        10/1988
JP        03200066        9/1991

OTHER PUBLICATIONS

Kim et al, Molecular Immunology, 32, 467-475, 1995.*
Comp, et al. 1984. "Determination of functional levels of protein C, an antithrombotic protein, using thrombin-thrombomodulin complex," *Blood* 63:15-21.
Esmon, C.T. "Natural anticoagulants and their pathways," *Handbook of Experimental Pharmacology*, (G.V.R. Born, P. Cuatrecasas, D. Ganten, H. Herken, K. Starke, and P. Taylor, eds), Springer-Verlag, New York, 1999; 132-447-476.
Faust, et al. 2001. "Molecular mechanisms of thrombosis in meningococcal septicaemia: the role of the protein C pathway in vivo," *Clinical Science*, London 101:19P (Abstr.), *2nd Annual Meeting of the British Infection Society*, London, Apr. 23, 1999 (Abstr.).
Gruber, A. and J.H. Griffin. 1992. "Direct detection of activated protein C in blood from human subjects," *Blood* 79:2340-2348.
Mesters, et al. 2000. "Prognostic value of protein C concentrations in neutropenic patients at high risk of severe septic complications," *Crit Care Med* 28:2209-2216.
Taylor, et al. 2001. "Endothelial cell protein C receptor plays an important role in protein C activation in vivo," *Blood* 97:1685-1688.
White, et al. 2000. "An open-label study of the role of adjuvant hemostatic support with protein C replacement therapy in purpura fulminans-associated meningoccernia," *Blood* 96:3719-3724.
Yans, S.B. and J.F. Dhainaut. 2001. "Activated protein C versus protein C in severe sepsis," *Crit Care Med* 29:S69-74.

* cited by examiner

*Primary Examiner*—David Saunders
(74) *Attorney, Agent, or Firm*—Eugenia S. Hansen; Conley Rose, P.C.

(57) ABSTRACT

A highly specific monoclonal antibody, produced by a hybridoma cell has been found. A new assay, highly specific for activated protein C (APC) has been developed which will permit rapid determination of APC levels in clinical situations.

44 Claims, 4 Drawing Sheets

ASSAY FOR RAPID DETECTION OF HUMAN ACTIVATED PROTEIN C AND HIGHLY SPECIFIC MONOCLONAL ANTIBODY THEREFOR

CROSS-REFERENCE TO RELATED APPLICATIONS

This application claims the benefit of International Application Ser. No. PCT/US01/30802, filed Oct. 2, 2001 which claims the benefit of U.S. Ser. No. 60/237,481, filed Oct. 2, 2000.

TECHNICAL FIELD OF THE INVENTION

This invention relates to measurement of activated protein C (APC) in clinical samples.

BACKGROUND

Protein C is the precursor to activated protein C (APC), a potent natural anticoagulant. Protein C is activated by thrombin in complex with thrombomodulin (TM). The activation is augmented by endothelial cell protein C receptor (EPCR). TM and EPCR can be down-regulated due to inflammatory mediators, such as tumor necrosis factor, reviewed by Esmon (Esmon, C. T., "Natural anticoagulants and their pathways," Handbook of Experimental Pharmacology 132:447–76; G. V. R. Born, Cuatrecasas, P., Ganten, D., Herken, H., Starke, K., and Taylor, P., eds., Springer-Verlag, New York 1999). TM and EPCR have also been found to be reduced in some forms of septic shock, meningococcemia in particular. Since EPCR and TM are expressed on endothelium, it is not possible to directly determine how well they are functioning without removal of blood vessels.

An alternative is to measure the levels of APC in circulation. Circulating APC levels can be measured with an enzyme capture assay. In this procedure, antibodies directed against protein C that cross react with APC are used to adsorb the protein C/APC from plasma. The antibodies can be coupled to affinity beads (Comp, P. C., R. R. Nixon, and C. T. Esmon. 1984. "Determination of protein C, an antithrombotic protein, using thrombin-thrombomodulin complex," Blood 63:15–21), or placed on a plastic microtiter plate (Gruber, A. and J. H. Griffin. 1992., "Direct detection of activated protein C in blood from human subjects," Blood 79:2340–48). The APC levels are also proportional to the protein C concentration in the plasma and to the thrombin concentration. The thrombin generation can be assessed either by measuring prothrombin fragment 1–2 levels or thrombin-antithrombin complex levels using ELISA based assays or radio-immuno assays. Protein C levels can be determined either by ELISA or a variety of functional assays that are commercially available.

Knowledge of the circulating levels of APC is important in evaluating the status of critically ill patients. Recently, APC has been shown to be effective in the treatment of septic shock. Previous studies have shown a correlation between decreases in protein C levels in septic patients and a negative clinical outcome (e.g., death, amputation, and organ failure). There are many clinical reports that supplementation with protein C can improve clinical outcome in patients with sepsis, particularly meningococcemia. (Yan, S. B. and J. F. Dhainaut. 2001. "Activated protein C versus protein C in severe sepsis," Crit Care Med 29:S69–74; Mesters, R. M., J. Helterbrand, B. G. Utterback, B. Yan, Y. B. Chao, J. A. Fernandez, J. H. Griffin and D. L. Hartman. 2000. "Prognostic value of protein C concentrations in neutropenic patients at high risk of severe septic complications," Crit Care Med 28:2209–2216; White, B., W. Livingstone, C. Murphy, A. Hodgson, M. Rafferty and O. P. Smith. 2000. "An open-label study of the role of adjuvant hemostatic support with protein C replacement therapy in purpura fulminans-associated meningococcemia," Blood 96:3719–372400. We have found that in some meningococcemia patients, supplementation with protein C failed to elicit detectable APC generation, indicating that the protein C activation mechanism was compromised. This is consistent with the observation that the EPCR and TM levels were reduced on the vasculature (Faust, S. N., R. S. Heyderman, O. Harrison, R. D. Goldin, Z. Laszik, C. T. Esmon, and M. Levin, "Molecular mechanisms of thrombosis in meningococcal septicaemia: the role of the protein C pathway in vivo," 2nd Annual Meeting of the British Infection Society, London, Apr. 23, 1999 (Abstr.)).

It would be very useful to be able to measure circulating APC, especially in clinical situations where a decision to use protein C versus APC in therapy needs to be expeditiously made, within a matter of hours at most. The currently available enzyme capture assay for APC using the microtiter plates is not useful for this purpose since the assay may take up to three weeks to develop. The major reasons for the very long times required in the enzyme capture assay are the low levels of circulating APC (about 3 ng/ml plasma) in normal individuals and the very high concentration of protein C (about 3000 ng/ml plasma) relative to the enzyme (Gruber, A. and J. H. Griffin. 1992., "Direct detection of activated protein C in blood from human subjects," Blood 79:2340–48). With the relatively low capacity of the microtiter plates used in the assay, the plasma must be diluted approximately 30 fold or more to allow capture of most of the protein C and APC. This problem could be circumvented if the capture antibody exhibited a high degree of specificity toward APC.

We have now developed an antibody (hereinafter referred to as "HAPC 1555") having a high degree of specificity toward APC. The antibody can detect APC in plasma within one hour, thus making the direct detection of APC practical clinically. Such antibodies can be adsorbed to surfaces including but not limited to microtiter plates. The antibody of the present invention exhibits improved capacity for APC, thus providing an improved assay for APC.

SUMMARY OF THE INVENTION

In one aspect, the invention is a hybridoma cell having the designation HAPC 1555 having been deposited under ATCC accession number PTA-2658.

In another aspect, the invention is a monoclonal antibody produced by a hybridoma cell HAPC 1555 having been deposited under ATCC accession number PTA-2658.

In another aspect, the invention is a binding fragment of the monoclonal antibody produced by hybridoma cell HAPC 1555 having been deposited under ATCC accession number PTA-2658, the binding segment capable of binding activated protein C with high selectivity over protein C. The binding fragment may comprise an Fab portion or Fc portion of the antibody.

In another aspect, the invention is an assay for assessing the concentration of activated protein C comprising testing a human plasma sample suspected of containing a quantity of activated protein C for binding to an antibody or portion thereof having high specificity for binding to APC, wherein the antibody is produced by hybridoma cell HAPC 1555 having been deposited under ATCC accession number PTA-2658.

In another aspect, the invention is an assay for the detection of activated protein C (APC) in a patient plasma sample comprising binding antibody HAPC 1555 or a portion thereof to a solid support to form a surface-bound antibody, contacting the surface-bound antibody with a patient plasma sample in a reaction zone, incubating the reaction zone under conditions effective for binding APC from the patient plasma sample to the surface-bound antibody, washing the reaction zone to remove unbound reactants, and testing the reaction zone for bound APC. In one embodiment, the patient plasma sample is prepared with a reversible active site inhibitor of APC. In a preferred assay, the patient plasma sample is about 20 mM benzamidine, 2 units per ml heparin, and 10 mM calcium. In another embodiment, the solid support comprises a surface suitable for binding antibodies with sufficient affinity so that reactants can be introduced to the reaction zone comprising the surface-bound antibody and removed without removal of the surface-bound antibody. Exemplary solid supports useful in the assay include microtiter plates, hollow fibers, affinity resins and beads. In the assay of the present invention, the reaction zone can be tested for bound APC by providing a saturating amount of substrate for APC to the reaction zone and detecting the activity of APC by monitoring any product formed which is indicative of the action of APC on the substrate. The substrate can be chromogenic, wherein the product is spectrophotometrically measured. Alternatively, the substrate can be fluorogenic, wherein the product is monitored with a fluorescence detection instrument.

BRIEF DESCRIPTION OF THE DRAWINGS

" FIG. 1A depicts overlaid dose-response binding curves generated with APC, at concentrations of 8.1 nM, 16 nM, 48.4 nM, and 68.5 nM, over an HAPC 1555-coated surface. FIG. 1B depicts overlaid dose-response binding curves generated with protein C, at concentrations of 35 nM, 69 nM, 137 nM, and 274 nM, over an HAPC 1555-coated surface.

FIG. 4A depicts amidolytic activity of APC at various times (from 0 to 21.6 hours). In FIG. 4B, the graph is magnified to show the amidolytic activity of low concentrations of APC.

DETAILED DESCRIPTION

Figure 1A:
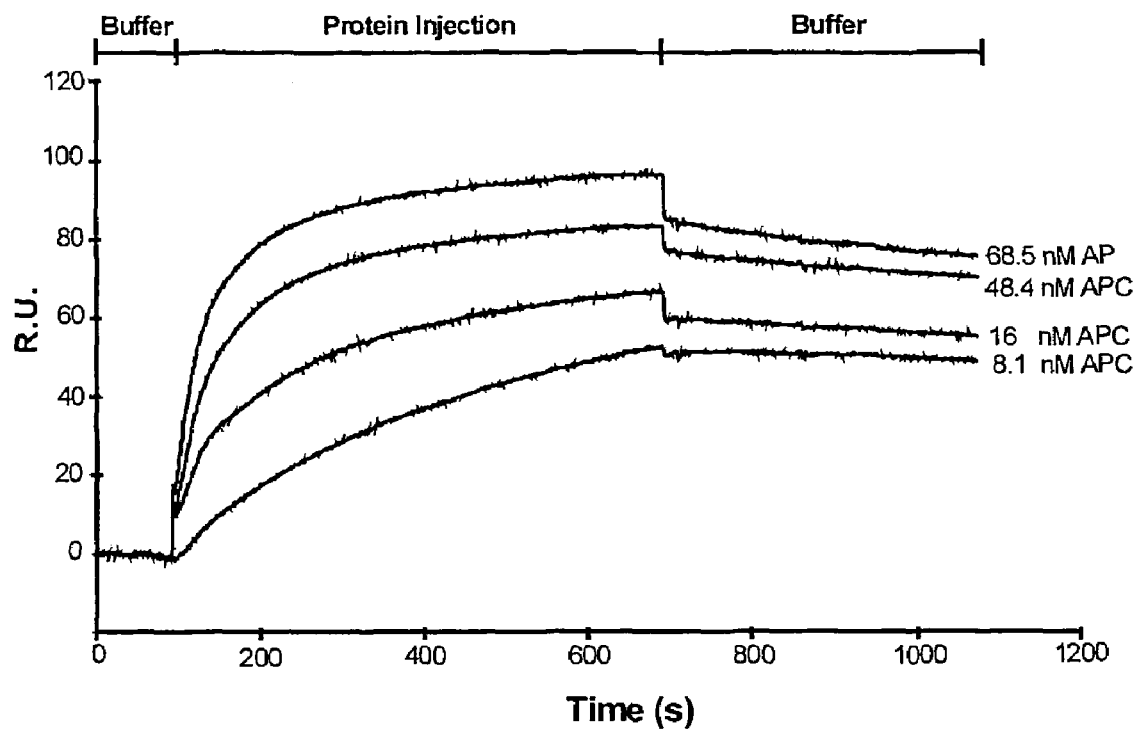
FIGS. 1A and 1B depict the surface plasmon resonance analysis of the interaction between APC or protein C and HAPC 1555. Approximately 680 RUs of HAPC 1555 was immobilized onto a carboxymethyl dextran sensor chip, and the kinetics of APC or protein C association with HAPC 1555 was monitored in the presence of 3 mM $CaCl_2$ at a flow rate of 10 μl/min as described under "Experimental Procedures.

A mouse hybridoma cell line has been established and given the designation HAPC 1555. The HAPC 1555 cell line was deposited under the provisions of the Budapest Treaty with the American Type Culture Collection (ATCC), 10801 University Boulevard, Manassas, Va. 20110-2209 on Nov. 7, 2000, and has been given the ATCC designation PTA-2658. The HAPC 1555 mouse hybridoma cell line was derived from BALB/C mouse spleen cells and myeloma cell line P3X63AG8-653. This cell line produces the monoclonal antibody we have designated as HAPC 1555, and the isotype of the antibody produced is IgG I kappa. The cell line can be grown utilizing standard culturing techniques, with RPMI 1640 and 10% bovine calf serum (with appropriate antibiotics) as an acceptable culture and storage medium.

Large-scale production of the monoclonal antibody HAPC 1555 was accomplished by growing cell line HAPC 1555 in serum-free medium in roller bottles. Purification of HAPC 1555 was accomplished by loading filtered media on MEP Hyper-Cel resin (Gibco, BRL), washing with 4 column volumes of TBS and eluting with 50 mm sodium acetate, pH 4.0. After reading the absorbance at 280 nanometers, the peak fractions were pooled and dialyzed against 10 mM MOPS, 0.1 M NaCl and frozen for later use.

The monoclonal antibody HAPC 1555 has been shown to have high specificity with respect to binding to activated protein C ("APC"). Thus, it can be used in assays to detect APC in a patient sample, using any methodology known in the art which employs specific antibodies for detection of proteins. An example of such an assay is given in Example 1. It is preferred that HAPC 1555 be bound to a solid support and incubated with a patient plasma sample suspected of containing APC in a reaction zone. Because of the high specificity of HAPC 1555, APC in the patient plasma sample will bind with the immobilized HAPC 1555, and other substances in the reaction zone can be washed away. An appropriate substrate for APC can then be added to the reaction zone to determine if any APC has bound to the HAPC 1555. Such reactions are well documented.

Because the monoclonal antibody HAPC 1555 does not interfere with the activity of APC, any direct assay for APC can be used to detect and quantitate APC. There are several comniercially-available kits and systems for this purpose. A suitable chromogenic substrate for the determination of APC is Spectrozyme PCa, available from American Diagnostica (Greenwich, Conn.). There are other substrates available which are either chromogenic or fluorogenic which can also be used. The important factor in choosing a substrate is that APC acts upon it to cleave a leaving group that emits a detectable signal.

In working with plasma samples, it is desirable to prepare plasma with standard citrate anticoagulant. To the plasma, a reversible inhibitor of APC should be added in order to prevent the covalent inhibition of APC by plasma proteinase inhibitors, for example, alpha-1-antitrypsin and protein C inhibitor. A preferred reversible inhibitor of APC is benzamidine, but any reversible active site inhibitor of APC can be used. An excess amount of the inhibitor is used, and this is determined by published values on the possible amount of APC that could be present in a given sample. An appropriate amount of benzamidine to use is about 20 mM. The plasma sample is also desirably prepared with a substance to prevent clotting of recalcified plasma, and heparin is conveniently used for this purpose in an amount to accomplish this purpose. It has been found that 2 units per ml of heparin provides the desired functionality, but other amounts can be used if they also do so. It is also desirable to add a source of calcium ions to the plasma preparation, and calcium chloride is conveniently used for this purpose. Calcium levels can vary as long as they are in excess of the citrate anticoagulant.

In the assay of the present invention, it is not necessary to dilute the plasma sample to be tested, which is an advantage over other assays reported prior to the present invention. The ability to use the plasma sample without or with minimal dilution provides a rapidity to the analysis of APC, permitting analysis in a matter of just less than an hour to several hours as opposed to up to three weeks for previously reported enzyme capture assay for APC. It is expected that the quantitation of APC can be made known to the clinician very rapidly, therefore permitting selection of appropriate therapy for the patient.

The HAPC 1555 antibody can also be used for protein purification, as a laboratory reagent where it is desirable to bind APC, and for other utilities for which a specific antibody is appropriate.

Characterization of HAPC 1555

A. Affinity Studies

Surface plasmon resonance (SPR) was used to measure the affinity of binding of HAPC 1555 to human activated protein C (APC) and human protein C. Real time biomolecular interactions between APC/protein C and HAPC 1555 were studied using a BIAcore™ 1000 biosensor instrument (BIAcore International AB, Uppsala, Sweden). HAPC 1555 was covalently coupled to a carboxymethyl dextran (CM5) sensor chip through its primary amine groups according to the manufacturer's instructions. Binding of APC or protein C to immobilized HAPC 1555 was monitored by measuring changes in RU (1000 RU corresponds to ≈1 ng of bound protein/mm$^2$). Unless otherwise stated, all experiments were performed at 25° C. at a flow rate of 10 $\mu$l/min in 20 mM Hepes, pH 7.5, 150 mM NaCl, 3 nM CaCl$_2$, and 0.005% surfactant P-20 (BIAcore grade, BIAcore International AB, Uppsala, Sweden).

For each set of experiments, the proteins were introduced onto the surface of a sensor chip that lacked inmmobilized HAPC 1555 (control sensor chip). The sensograms of the control sensor chip were subtracted from the sensograms of the HAPC 1555-containing flowcells to remove the effects of nonspecific binding to the dextran surface. After each protein injection, the sensor chips were regenerated by the injection of 20 $\mu$l of 1M glycine pH 2.5, followed by washing for 3 min with buffer before reinjecting APC for the next cycle.

Figure 1B:
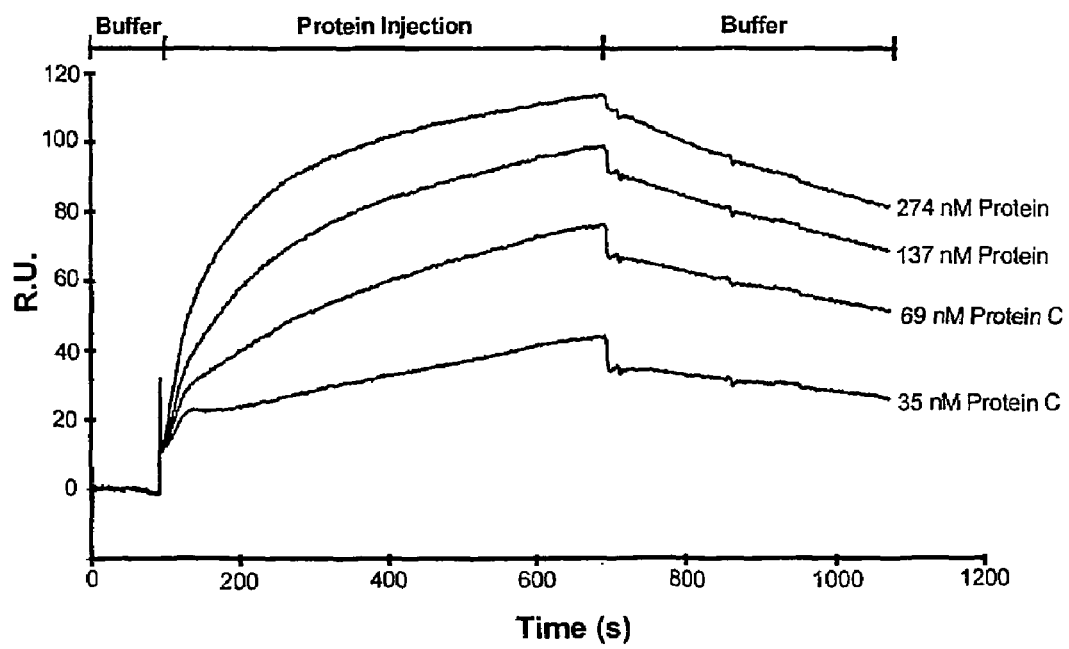

The interaction between APC or protein C and HAPC 1555 was monitored by flowing various concentrations of APC (from 8.1 nM to 68.5 nM) or protein C (from 35 nM to 274 nM) over a sensor chip containing immobilized HAPC 1555. The overlaid dose-response binding curves for APC and protein C are shown in FIGS. 1A and 1B, respectively. To determine the $K_d$ values for the interaction between APC or protein C and HAPC 1555, the maximum RUs of the binding isotherms shown in FIGS. 1A and 1B were plotted versus APC or Protein C concentration. The $K_d$ values were calculated by non-linear regression analysis of the curves. The $K_d$ value of APC binding to HAPC 1555 was calculated as $K_d$=6.2±0.9 nM, whereas the affinity of protein C for HAPC 1555 was approximately 10-fold lower ($K_d$=65±3 nM). Each $K_d$ value represents the mean and standard deviation of two separate surface plasmon resonance binding studies. In the absence of CaCl$_2$, there is no binding of APC nor protein C to immobilized HAPC 1555.

Figure 2:
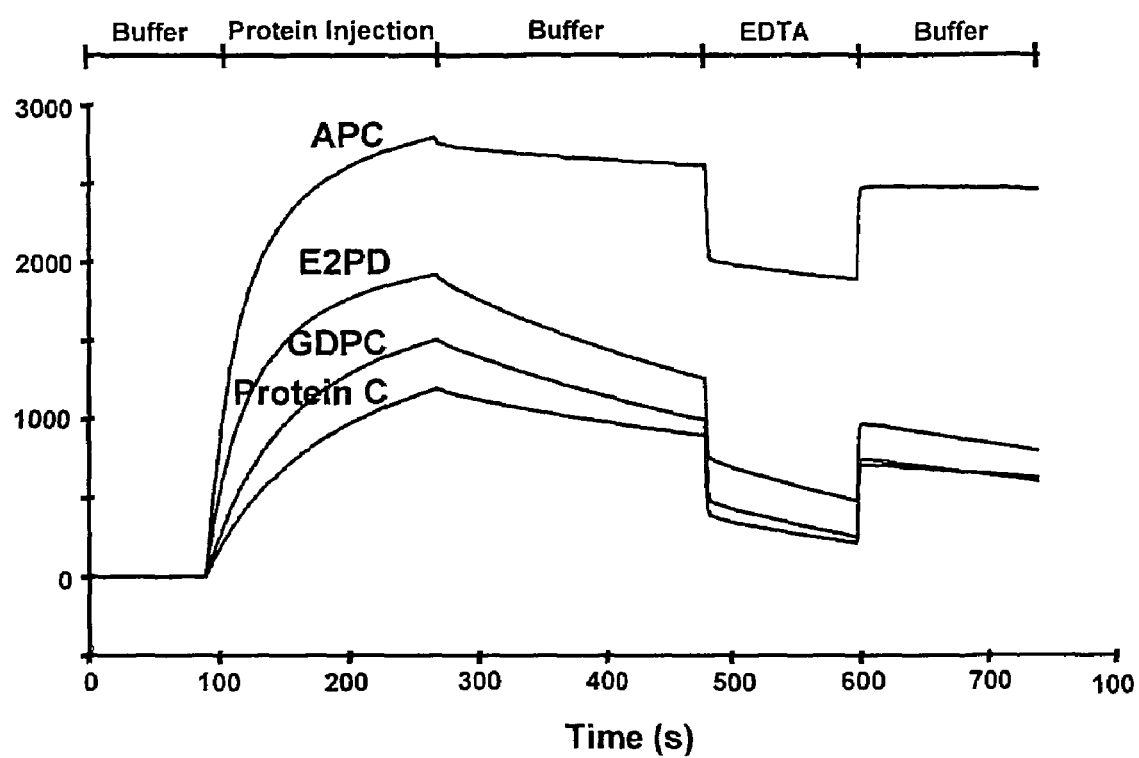
FIG. 2 depicts surface plasmon resonance analysis of the binding of APC, protein C, GDPC, and E2PD to HAPC 1555. The association of 250 nM of APC, protein C, GDPC, or E2PD with immobilized HAPC 1555 (≈8000 RU) was monitored in the presence of 3 mM $CaCl_2$ at a flow rate of 10 μl/min as described under "Experimental Procedures." Protein binding was unaffected by the injection of 20 μl of 5 mM EDTA.

To localize the HAPC 1555 binding domain on APC/protein C, surface plasmon resonance binding studies were performed using two protein C derivatives: (a) GDPC, i.e., Gla-domainless protein C, and (b) E2PD, i.e., protein C lacking the Gla-domain and the first EGF domain. As shown in FIG. 2, both derivatives bind to immobilized HAPC 1555, suggesting that the HAPC 1555 binding domain on APC/protein C is localized in the protease domain and/or the EGF-2 domain. Although the interaction of APC, protein C, GDPC, and E2PD with immobilized HAPC 1555 requires the presence of CaCl$_2$, dissociation of bound ligands was not achieved by the addition of 5 mM EDTA (FIG. 2).

B. Effect on APC Amidolytic Activity

The chromogenic activity of 5 mM APC in 20 mM Hepes, pH 7.5, 150 mM NaCl, 5 mM CaCl$_2$, 0.5% (w/v) gelatin was determined with 0 to 1 mM Spectrozyme PCa (American Diagnostica, Greenwich Conn.) in the absence or presence of 400 nM of HAPC 1555. A 50 $\mu$l aliquot of reaction solution was mixed with 50 $\mu$l of chromogenic substrate on a microtiter plate, and the change in absorbance with time at 405 nm was determined on a Vmax microplate reader (Molecular Devices Corp., Sunnyvale, Calif.). All samples were assayed in duplicate. The $K_m$ values were calculated by nonlinear regression analysis using the Michaelis-Menten equation in *Tablecurve* (Jandel Scientific, San Rafael, Calif.).

Figure 3:
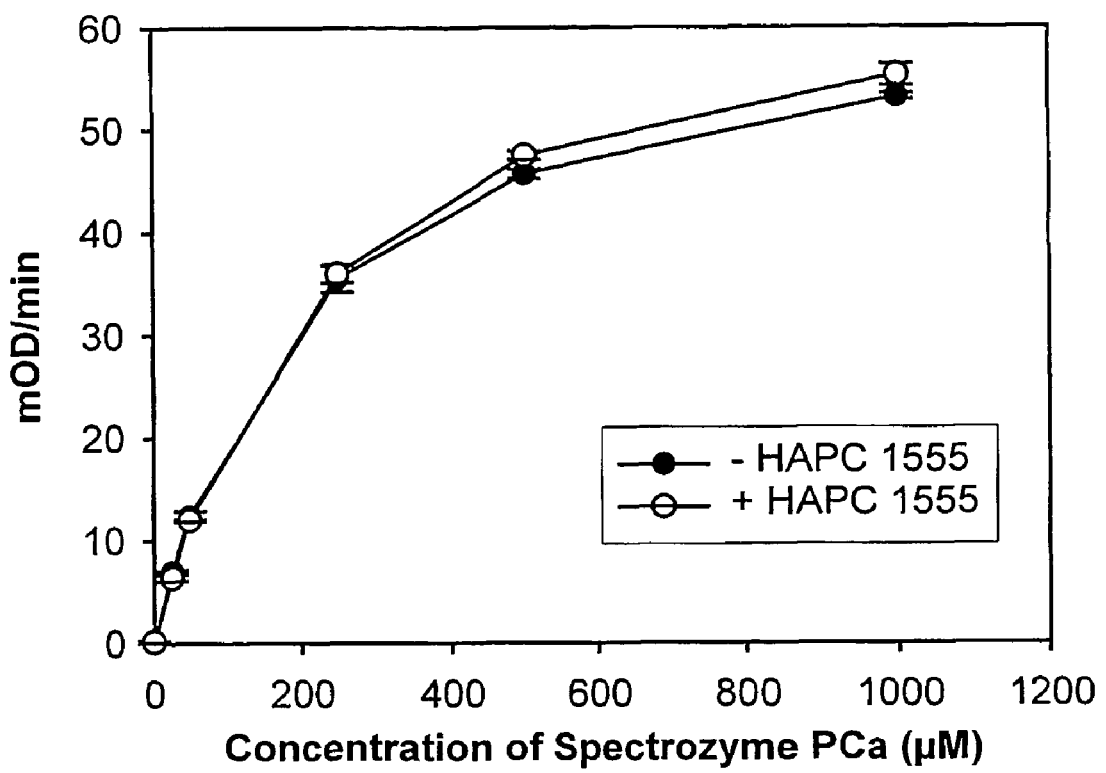
FIG. 3 depicts the effect of HAPC 1555 on the amidolytic activity of APC. The chromogenic activity of APC was determined with 0 to 1 mM of Spectrozyme PCa in the absence or presence of 400 nM HAPC 1555. The $K_m$ and $k_{cat}$ values were calculated by non-linear regression analysis using the Michaelis-Menten equation. The values correspond to the mean and standard deviation of at least two determinations.

The effect of HAPC 1555 on the rate of APC-mediated hydrolysis of Spectrozyme PCa is shown in FIG. 3. The results show that the kinetic parameters of APC toward the synthetic substrate are not affected by the presence of HAPC 1555. Thus, it is possible to utilize HAPC 1555 to quantitate APC levels in human plasma using an enzyme capture assay.

EXAMPLE 1

Quantification of APC in Human Plasma Using HAPC 1555

A. Methods

Initially, 96-well vinyl microtiter plates (Costar, Cat # 2596) were coated with 100 $\mu$l of HAPC 1555 (5 $\mu$g/ml) in coating buffer (20 mM Hepes, pH 7.5, 150 mM NaCl, 5 mM CaCl$_2$) for 2 hours at 37° C. As negative controls, microtiter plate wells were coated with either 5 $\mu$g/ml HPC4 monoclonal antibody or 1% bovine serum albumin (BSA) in the same buffer. The plates were then blocked for 1 hour at 37° C. or overnight at 4° C. with 200 $\mu$l of blocking buffer (coating buffer containing 1% BSA). The solutions were gently removed from the plates by vacuum.

To generate a standard curve for the quantitative measurement of APC in plasma, increasing amounts of APC (from 0 to 250 ng/ml) were spiked into normal pooled plasma containing 20 mM Hepes, pH 7.5, 2 units/ml heparin, 20 mM benzamidine, and 10 mM CaCl$_2$. The spiked plasma (100 $\mu$l) were transferred to the plates and incubated at room temperature for 1 hour. The wells were then washed three times with wash buffer (20 mM Hepes, pH 7.5, 150 mM NaCl, 0.05% Tween-20, and 5 mM CaCl$_2$). The chromogenic activity of APC was determined by the addition of 100 μl of Spectrozyme PCa (1 mM) in 20 mM Hepes, pH 7.5, 150 mM NaCl, 5 mM $CaCl_2$. The plates were immediately placed at 37° C., and substrate hydrolysis was monitored at 405 nm over time using a Vmax microplate reader (Molecular Devices Corp, Sunnyvale, Calif.). All samples were assayed in duplicates or triplicates.

Figure 4A:
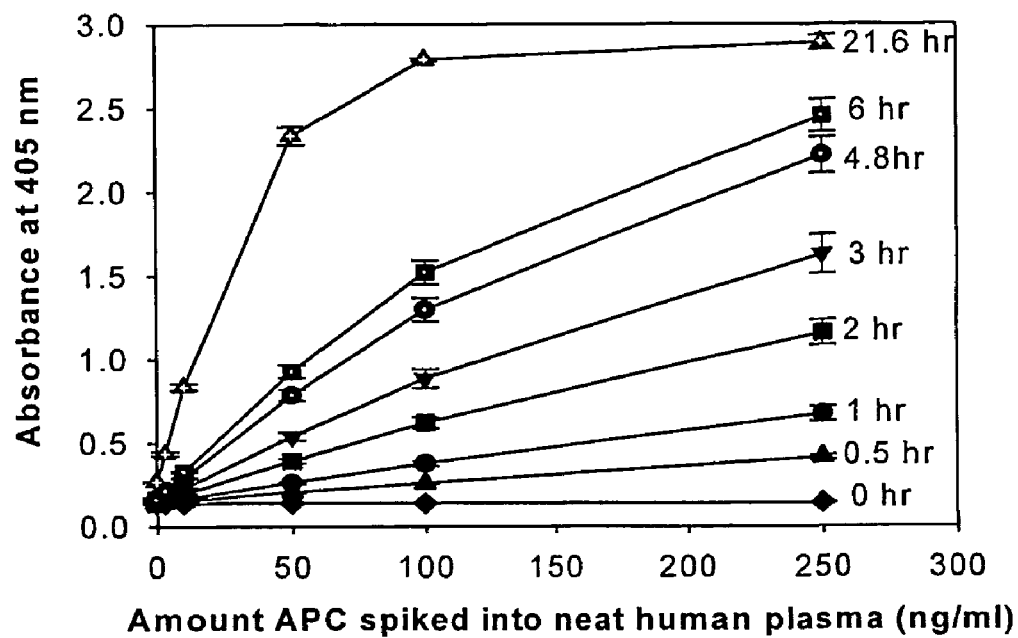
FIGS. 4A and 4B depict APC standard curves in enzyme capture assays. Increasing amounts of APC (0 to 250 ng/ml) were spiked into normal pooled plasma containing 20 mM Hepes, pH 7.5, 2 units/ml heparin, 20 mM benzamidine, and 10 mM $CaCl_2$. The samples were incubated in microtiter wells containing bound HAPC 1555.
Figure 4B:
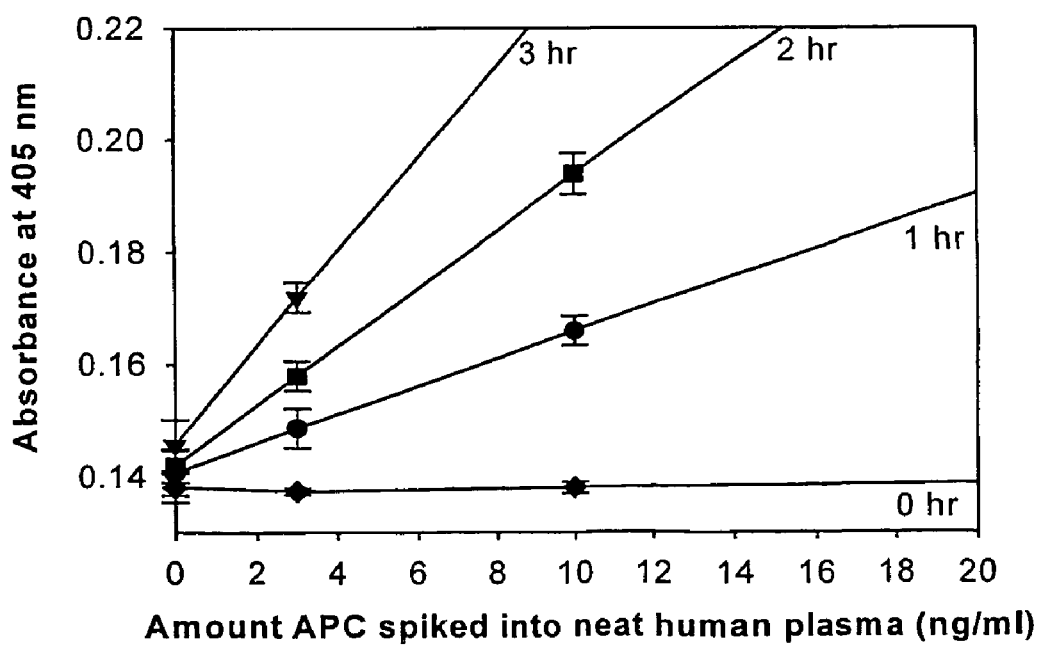

The APC enzyme capture assay is useful to quantitate APC levels in human plasma. As shown in FIG. 4, the assay is sensitive to plasma APC levels of ≦3 ng/ml with an incubation time of 1 hour. Substrate hydrolysis was linear for concentrations ranging from 0 to 100 ng/ml at incubation times of up to approximately 6 hours. Further, measured APC in plasma did not vary when protein C concentration varied from 0 to 200% of normal (data not shown).

The specificity of the HAPC 1555 antibody was further confirmed by the results obtained from the plate wells set up as the negative controls. When HPC4 (an anti-protein C monoclonal antibody) or BSA was coated on the microtiter wells, the chromogenic activity of the APC-spiked plasma was reduced to background.

As further confirmation of the specificity of HAPC 1555, APC-spiked plasma was pre-incubated with 300 nM of HAPC 1555 and used instead of plasma samples not subjected to pre-incubation in the assay described above. It was found that use of pre-incubated APC-spiked plasma resulted in a measure of amidolytic activity essentially equivalent to that of background. This indicates that the pre-incubated APC-spiked plasma did not bind to the wells coated with HAPC 1555 due to saturation of the binding sites with the HAPC 1555 added to the plasma. After washing of the reaction zone, no bound APC was present to exhibit chromogenic activity in the presence of the substrate.

EXAMPLE 2

Quantification of APC in Human Plasma Specimens

The procedure of Example 1 can be used to test human plasma for APC. In Example 1, human plasma was spiked with APC, but to assess a clinical specimen for its APC content, a specimen is collected from the patient in standard citrate anticoagulant that also contains 20 mM benzamidine HCl. The blood cells are removed by centrifugation using standard techniques. The plasma is used in the assay after standard preparation (e.g., 20 mM Hepes, pH 7.5, 2 units/ml heparin and 10 mM $CaCl_2$). The plasma sample is then analyzed for APC using an assay such as described in Example 1.

Indications Relating to Deposited Microorganism or Other Biological Material

A mouse hybridoma cell line useful in the assay of the present invention has been established and given the designation HAPC 1555. The HAPC 1555 cell line was deposited under the provisions of the Budapest Treaty with the American Type Culture Collection (ATCC), 10801 University Boulevard, Manassas, Va. 20110-2209 on Nov. 7, 2000, and has been given the ATCC designation PTA-2658. The HAPC 1555 mouse hybridoma cell line was derived from BALB/C mouse spleen cells and myeloma cell line P3X63AG8-653. This cell line produces the monoclonal antibody we have designated as HAPC 1555, and the isotype of the antibody produced is IgG I kappa. The cell line can be grown utilizing standard culturing techniques, with RPMI 1640 and 10% bovine calf serum (with appropriate antibiotics) as an acceptable culture and storage medium.

We claim:

1. A hybridoma cell, having the designation HAPC 1555 having been deposited under ATCC accession number PTA-2658.

2. A monoclonal antibody produced by a hybridoma cell HAPC 1555 having been deposited under ATCC accession number PTA-2658.

3. A binding fragment of the monoclonal antibody produced by hybridoma cell HAPC 1555 having been deposited under ATCC accession number PTA-2658, said binding segment capable of binding activated protein C with high selectivity over protein C.

4. The binding fragment of claim 3, comprising an Fab portion of said antibody.

5. An assay for assessing the concentration of activated protein C comprising testing a human plasma sample suspected of containing a quantity of activated protein C for binding to an antibody or portion thereof having high specificity for binding to activated protein C, said antibody produced by hybridoma cell HAPC 1555 having been deposited under ATCC accession number PTA-2658.

6. An assay for the detection of activated protein C in a patient plasma sample, comprising:
binding an antibody produced by hybridoma cell HAPC 1555, said cell having been deposited under ATCC accession number PTA 2658, or a binding fragment of said antibody, to a solid support to form a surface-bound antibody,
contacting said surface-bound antibody with a patient plasma sample in a reaction zone;
incubating said reaction zone under conditions effective for binding activated protein C from said patient plasma sample to said surface-bound antibody;
washing said reaction zone to remove unbound reactants; and
testing said reaction zone for bound activated protein C.

7. The assay of claim 6, wherein said patient plasma sample is prepared with a reversible active site inhibitor of activated protein C.

8. The assay of claim 7, wherein said patient plasma sample is about 20 mM benzamidine, 2 units per ml heparin, and 10 mM calcium.

9. The assay of claim 6, wherein said solid support comprises a surface suitable for binding antibodies with sufficient affinity so that reactants can be introduced to said reaction zone comprising said surface-bound antibody and removed without removal of said surface-bound antibody.

10. The assay of claim 9, wherein said solid support is selected from microtiter plates, hollow fibers, affinity resins and beads.

11. The assay of claim 7, wherein said solid support comprises a surface suitable for binding antibodies with sufficient affinity so that reactants can be introduced to said reaction zone comprising said surface-bound antibody and removed without removal of said surface-bound antibody.

12. The assay of claim 11, wherein said solid support is selected from microtiter plates, hollow fibers, affinity resins and beads.

13. The assay of claim 8, wherein said solid support comprises a surface suitable for binding antibodies with sufficient affinity so that reactants can be introduced to said reaction zone comprising said surface-bound antibody and removed without removal of said surface-bound antibody.

14. The assay of claim 13, wherein said solid support is selected from microtiter plates, hollow fibers, affinity resins and beads.

15. The assay of claim 5, wherein said reaction zone is tested for bound activated protein C by providing a saturating amount of substrate for activated protein C to said reaction zone and detecting the activity of activated protein C by monitoring any product formed which is indicative of the action of activated protein C on said substrate.

16. The assay of claim 15, wherein said substrate is chromogenic, and said product is spectrophotometrically measured.

17. The assay of claim 15, wherein said substrate is fluorogenic, and said product is monitored with a fluorescence detection instrument.

18. The assay of claim 6, wherein said reaction zone is tested for bound activated protein C by providing a saturating amount of substrate for activated protein C to said reaction zone and detecting the activity of activated protein C by monitoring any product formed which is indicative of the action of activated protein C on said substrate.

19. The assay of claim 18, wherein said substrate is chromogenic, and said product is spectrophotometrically measured.

20. The assay of claim 18, wherein said substrate is fluorogenic, and said product is monitored with a fluorescence detection instrument.

21. The assay of claim 7, wherein said reaction zone is tested for bound activated protein C by providing a saturating amount of substrate for activated protein C to said reaction zone and detecting the activity of activated protein C by monitoring any product formed which is indicative of the action of activated protein C on said substrate.

22. The assay of claim 21, wherein said substrate is chromogenic, and said product is spectrophotometrically measured.

23. The assay of claim 21, wherein said substrate is fluorogemc, and said product is monitored with a fluorescence detection instrument.

24. The assay of claim 8, wherein said reaction zone is tested for bound activated protein C by providing a saturating amount of substrate for activated protein C to said reaction zone and detecting the activity of activated protein C by monitoring any product formed which is indicative of the action of activated protein C on said substrate.

25. The assay of claim 24, wherein said substrate is chromogenic, and said product is spectrophotometrically measured.

26. The assay of claim 24, wherein said substrate is fluorogenic, and said product is monitored with a fluorescence detection instrument.

27. The assay of claim 9, wherein said reaction zone is tested for bound activated protein C by providing a saturating amount of substrate for activated protein C to said reaction zone and detecting the activity of activated protein C by monitoring any product formed which is indicative of the action of activated protein C on said substrate.

28. The assay of claim 27, wherein said substrate is chromogenic, and said product is spectrophotometrically measured.

29. The assay of claim 27, wherein said substrate is fluorogenic, and said product is monitored with a fluorescence detection instrument.

30. The assay of claim 10, wherein said reaction zone is tested for bound activated protein C by providing a saturating amount of substrate for activated protein C to said reaction zone and detecting the activity of activated protein C by monitoring any product formed which is indicative of the action of activated protein C on said substrate.

31. The assay of claim 30, wherein said substrate is chromogenic, and said product is spectrophotometrically measured.

32. The assay of claim 30, wherein said substrate is fluorogenic, and said product is monitored with a fluorescence detection instrument.

33. The assay of claim 11, wherein said reaction zone is tested for bound activated protein C by providing a saturating amount of substrate for activated protein C to said reaction zone and detecting the activity of activated protein C by monitoring any product formed which is indicative of the action of activated protein C on said substrate.

34. The assay of claim 33, wherein said substrate is chromogenic, and said product is spectrophotometrically measured.

35. The assay of claim 33, wherein said substrate is fluorogenic, and said product is monitored with a fluorescence detection instrument.

36. The assay of claim 12, wherein said reaction zone is tested for bound activated protein C by providing a saturating amount of substrate for activated protein C to said reaction zone and detecting the activity of activated protein C by monitoring any product formed which is indicative of the action of activated protein C on said substrate.

37. The assay of claim 36, wherein said substrate is chromogenic, and said product is spectrophotometrically measured.

38. The assay of claim 36, wherein said substrate is fluorogenic, and said product is monitored with a fluorescence detection instrument.

39. The assay of claim 13, wherein said reaction zone is tested for bound activated protein C by providing a saturating amount of substrate for activated protein C to said reaction zone and detecting the activity of activated protein C by monitoring any product formed which is indicative of the action of activated protein C on said substrate.

40. The assay of claim 39, wherein said substrate is chromogenic, and said product is spectrophotometrically measured.

41. The assay of claim 39, wherein said substrate is fluorogenic, and said product is monitored with a fluorescence detection instrument.

42. The assay of claim 14, wherein said reaction zone is tested for bound activated protein C by providing a saturating amount of substrate for activated protein C to said reaction zone and detecting the activity of activated protein C by monitoring any product formed which is indicative of the action of activated protein C on said substrate.

43. The assay of claim 42, wherein said substrate is chromogenic, and said product is spectrophotometrically measured.

44. The assay of claim 42, wherein said substrate is fluorogenic, and said product is monitored with a fluorescence detection instrument.

* * * * *

UNITED STATES PATENT AND TRADEMARK OFFICE
CERTIFICATE OF CORRECTION

PATENT NO. : 6,989,241 B2
APPLICATION NO. : 10/398063
DATED : January 24, 2006
INVENTOR(S) : Charles T. Esmon, Patricia C. Y. Liaw and Gary L. Ferrell Page 1 of 1

It is certified that error appears in the above-identified patent and that said Letters Patent is hereby corrected as shown below:

Col. 4, line 52, replace " comniercially" with—commercially—
Col. 5, line 45, replace "3 nM $CaCl_2$" — 3 mM $CaCI_2$—
Col. 5, line 49 replace "inmobilized" with —immobilized—
Col. 9, line 38, replace "fluorogemc" with —fluorogenic—

Signed and Sealed this

Eighth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,989,241 B2
APPLICATION NO. : 10/398063
DATED : January 24, 2006
INVENTOR(S) : Charles T. Esmon, Patricia C. Y. Liaw and Gary L. Ferrell It is certified that error appears in the above-identified patent and that said Letters Patent is hereby corrected as shown below:

Col. 4, line 52, replace " comniercially" with—commercially—
Col. 5, line 45, replace "3 nM $CaCl_2$" — 3 mM $CaCl_2$—
Col. 5, line 49 replace "inmmobilized" with —immobilized—
Col. 9, line 38, replace "fluorogemc" with —fluorogenic—

This certificate supersedes Certificate of Correction issued August 8, 2006.

Signed and Sealed this

Eighth Day of May, 2007

JON W. DUDAS
*Director of the United States Patent and Trademark Office*